United States Patent
Bonnet (10) Patent No.: US 10,905,890 B2
(45) Date of Patent: Feb. 2, 2021

(54) AUTONOMOUS CARDIAC IMPLANT OF THE LEADLESS CAPSULE TYPE WITH ENERGY HARVESTER AND CONTROLLED-CHARGE ENERGY STORAGE BUFFER

(71) Applicant: CAIRDAC, Antony (FR)

(72) Inventor: Jean-Luc Bonnet, Massy (FR)

(73) Assignee: CAIRDAC, Antony (FR)

( * ) Notice: Subject to any disclaimer, the term of this patent is extended or adjusted under 35 U.S.C. 154(b) by 99 days.

(21) Appl. No.: 16/140,457

(22) Filed: Sep. 24, 2018

(65) Prior Publication Data

US 2019/0091479 A1    Mar. 28, 2019

(30) Foreign Application Priority Data

Sep. 22, 2017  (FR) ...................... 17 58769

(51) Int. Cl.
| | |
|---|---|
| *A61N 1/378* | (2006.01) |
| *A61N 1/39* | (2006.01) |
| *A61N 1/365* | (2006.01) |
| *A61N 1/375* | (2006.01) |
| A61B 5/042 | (2006.01) |
| H01L 41/053 | (2006.01) |
| A61N 1/372 | (2006.01) |
| H02N 2/18 | (2006.01) |

(52) U.S. Cl.
CPC ....... *A61N 1/3785* (2013.01); *A61N 1/36542* (2013.01); *A61N 1/3756* (2013.01); *A61N 1/3975* (2013.01); *A61B 5/0422* (2013.01); *A61N 1/37252* (2013.01); *H01L 41/053* (2013.01); *H02N 2/18* (2013.01)

(58) Field of Classification Search
CPC .............. A61N 1/3785; A61N 1/36542; A61N 1/3756; A61N 1/3975; A61N 1/37252; A61B 5/0422; H01L 41/053; H02N 2/18
USPC .......................................................... 607/35
See application file for complete search history.

(56) References Cited

U.S. PATENT DOCUMENTS

| | | | | |
|---|---|---|---|---|
| 2003/0040774 | A1* | 2/2003 | Terry, Jr. ............ | A61N 1/36114 607/2 |
| 2008/0021532 | A1* | 1/2008 | Kveen ................ | A61N 1/37288 607/115 |
| 2008/0300660 | A1* | 12/2008 | John .................... | A61N 1/3785 607/61 |
| 2013/0226260 | A1* | 8/2013 | Brenner .............. | A61N 1/3785 607/35 |

(Continued)

*Primary Examiner* — William J Levicky
*Assistant Examiner* — Alexander M Eisenberg
(74) *Attorney, Agent, or Firm* — Steven M. Greenberg, Esq.; Shutts & Bowen LLP (57) ABSTRACT

An energy harvester converts into electrical energy the external stresses applied to the implant at the heartbeat rhythm. This harvester comprises an inertial unit and a transducer delivering an electrical signal that is rectified and regulated for powering the implant and charging an energy storage component. The charge level of the energy storage component is compared with a lower threshold to detect an insufficient charge, and a dynamic charging control circuit modifies, as and whenever necessary, and if the current patient's state allows it, a stimulation parameter in a direction liable to increase in return the mean level of the mechanical energy that is produced and harvested.

15 Claims, 6 Drawing Sheets

(56) References Cited

U.S. PATENT DOCUMENTS

| | | | |
|---|---|---|---|
| 2013/0238073 A1* | 9/2013 | Makdissi | A61N 1/36542 |
| | | | 607/126 |
| 2013/0261497 A1* | 10/2013 | Pertijs | A61B 5/686 |
| | | | 600/549 |
| 2015/0094786 A1 | 4/2015 | Deterre et al. | |
| 2015/0174412 A1 | 6/2015 | Stahmann et al. | |
| 2016/0375250 A1* | 12/2016 | Bonnet | A61N 1/365 |
| | | | 607/59 |
| 2017/0232261 A1* | 8/2017 | Stadler | A61B 5/0422 |
| | | | 607/18 |

* cited by examiner

AUTONOMOUS CARDIAC IMPLANT OF THE LEADLESS CAPSULE TYPE WITH ENERGY HARVESTER AND CONTROLLED-CHARGE ENERGY STORAGE BUFFER

CROSS REFERENCE TO RELATED APPLICATIONS

This application claims priority under 35 U.S.C. § 119(a) to French Patent Application Serial Number 1758769, filed Sep. 22, 2017, the entire teachings of which are incorporated herein by reference.

BACKGROUND OF THE INVENTION

Field of the Invention

The invention relates to active implantable medical devices (AIMDs), in particular cardiac implants for monitoring the myocardium activity and delivering stimulation, resynchronization or defibrillation pulses in case of rhythm disorder detected by the device.

Description of the Related Art

The invention more particularly relates to those devices which incorporate a self-powering system including a mechanical energy harvesting device associated with an integrated energy storage component—it may be in particular a rechargeable battery or a high-performance capacitor. The harvesting device, also called harvester or scavenger, collects the mechanical energy resulting from the various movements undergone by the body of the implanted device. Those movements may have for origin a certain number of phenomena occurring at the rhythm of the heartbeats, in particular periodic shakings of the wall on which the implant is anchored, cardiac tissue vibrations related inter alia to the closings and openings of the cardiac valves, or blood flow rate variations in the surrounding environment, which stress the implant and make it oscillate at the rhythm of the flow rate variations. The mechanical energy collected by the harvester is converted into electrical energy (voltage or current), by means of a suitable mechanical-electrical transducer, for powering the various circuits and sensors of the device and for charging the energy storage component.

The energy harvesting technique is particularly well adapted for powering implanted autonomous capsules having no physical connection with a remote device. These capsules are called for this reason "leadless capsules", for distinguishing them from the electrodes or sensors arranged at the distal end of a lead, through the whole length of which run one or several conductors connected to a generator connected to the opposite, proximal end.

In the cardiac application case, they may be epicardial leadless capsules, fixed to the outer wall of the heart, or endocavitary capsules, fixed to the inner wall of a ventricular or atrial cavity, or capsules fixed to a wall of a vessel near the myocardium. The invention is nevertheless not limited to a particular type of capsule, and it is as well applicable to any type of leadless capsule, whatever the operational purpose thereof.

The attachment of the capsule to the implantation site is made using a protruding anchoring system extending the capsule body and intended to enter the cardiac tissue, in particular by means of a screw. The capsule moreover includes various electronic circuits, sensors, etc., as well as wireless communication emitter/receiver means for the remote exchange of data, all of them being integrated in a body of very small size that can be implanted into sites whose access is difficult or that leave little room, such as the ventricle apex, the inner wall of the atrium, etc. United States Patent Application Publication No. 2009/0171408 A1 by Solem describes various examples of such leadless intracardiac capsules.

In any case, the processing of the signals within the capsule and the remote transmission thereof requires a non-negligible energy with respect to the energetic resources that this capsule can store into a very small available volume. Now, taking into account its autonomous character, the capsule can only use its own resources, hence the necessity of an integrated self-powering system including an energy harvester combined to a small integrated energy storage component.

There exist several types of energy harvesters, based on different physical principles: system of the automatic wind-up watch movement type, mobile magnet system, bellows system or the like for collecting blood pressure variations, etc.

The invention more particularly relates to leadless capsules (or similar implantable devices) whose energy harvester uses an inertial unit subjected to the above-described external solicitations, with such an inertial unit. This inertial unit may in particular implement—but without limitation—a transducer coupled to a pendular mechanism including in the capsule a mobile mass, called "seismic mass" or "inertial mass". This inertial mass is driven according to the movements of the capsule, which is permanently subjected to the various external stresses described hereinabove. After each of these stresses, the inertial mass, which is coupled to an elastically deformable element, oscillates at a natural frequency of free oscillation.

Other types of inertial units for an energy harvester also show this oscillation phenomenon. In any case, the invention is not limited to a particular type of inertial unit, and covers not only the units with an electromechanical transducer but also those with a piezoelectric, electromagnetic, electrostatic or tribological transducer, all adapted to deliver an electrical signal under the effect of an external mechanical stress, and that will be denoted by the generic word "transducer".

The oscillation frequency of the inertial unit, typically of the order of a few tens of hertz, is in particular higher than the frequency of the external cyclic stresses that correspond to the heartbeat rate (at most a few hertz). Hence, at each cardiac contraction, the seismic mass (or another functionally similar mechanical component) will be stressed with a higher or lower amplitude, then the inertial system will oscillate several times with decreasing amplitudes (bounce characteristic of a damped periodic oscillation), and will finally stabilize up to the following heartbeat, where the stress/oscillations cycle will occur again in a comparable manner.

The mechanical energy of the inertial unit oscillation is for example converted into an electrical energy by a mechanical-electrical transducer producing an electrical signal. This signal is delivered to a power management circuit of the implant, which rectifies and regulates the electrical signal to deliver as an output a stabilized direct voltage or current, for powering the various electronic circuits and sensors of the implant, as well as for charging the energy storage component.

Advantageously, but without limitation, the mechanical-electrical transducer may be a piezoelectric component cyclically and alternately stressed in flexion so as to generate within the material that constitutes it electrical charges that are collected at the surface of the component to be used by the self-powering system of the capsule.

The piezoelectric component may for example be a piezoelectric plate fitted at one end and coupled to the inertial mass at the other end, which is free. Reference can be made in particular to European Patent Publication EP 2 857 064 A1 by Sorin CRM, which describes such an energy harvester arrangement, particularly suitable for powering a leadless capsule.

Published Patent Cooperation Treaty Request WO 2012/020034 A1 describes another energy harvester of this type, combined with an implantable capsule provided with external piezoelectric fins adapted to open out like an umbrella. The movement of these fins produces a voltage that, after rectification, is applied to a buffer capacitor designed to store the energy produced. The voltage across the capacitor terminals is monitored by a comparator, and, when this voltage reaches a predetermined upper limit, the charge of the capacitor is transferred to a voltage regulator used to power the implant with a stable voltage. When the voltage across the capacitor terminals reaches a predetermined lower limit, then the regulator is uncoupled from the capacitor to allow again the accumulation of energy within the latter.

Insofar as powering such a device depends on a rechargeable element, it is vital that the charge level of the latter be always sufficient to allow a correct operation of the device in any circumstances, and with a reserve of energy guaranteeing this operation, even for extended periods in which the charge would be lower.

Now, the studies of the in vivo behavior of the autonomous implants self-powered by an energy harvester demonstrate that, independently from the conversion efficiency of the energy harvester, the charging effectiveness may vary as a function of many external factors, specific to the patient.

In particular, a reduced cardiac activity, characterized for example by a slow rhythm, bad hemodynamics causing a low blood flow rate, poor contractility of the myocardium with wall movements of low amplitude, etc., may lead to critical situations in which the electrical energy produced by the energy harvester would be insufficient to power the electronic circuit of the implant and, a fortiori, to charge the energy storage component that would progressively empty, risking a complete exhaustion.

By the way, it will be noted that these situations of deteriorated critical state of the patient are precisely those in which the circuits of the implant are the most urged, due to the need to generate and deliver quasi-permanently stimulation pulses at a relatively high level, to call on the processor for complex calculations for diagnosing the patient state and for regulating the therapy applied, to operate radiofrequency emitting/receiving circuits for the exchange of data with other implants or with a remote device or equipment, etc. The consumption of the electronic unit of the implant (electronic circuits, digital processors, sensors) may hence be relatively high in such situations in which, precisely, the mechanical energy collected by the energy harvester may be relatively low, or even insufficient.

Such is the problem of the invention, which is to anticipate such situations of insufficient charging of the energy storage component and to remedy it so as to be able to guarantee in any circumstances a satisfying power supply of the implant.

BRIEF SUMMARY OF THE INVENTION

The basic idea of the invention lies in monitoring the charge level of the energy storage component, and, if this level falls below a minimum threshold, acting on the myocardium stimulation so as to cause a controlled increase of the mechanical energy produced by the contractions of the latter, provided of course that the state in which the patient is at that time allows it. The increased mechanical activity of the myocardium will then allow collecting a correlatively higher energy, sufficient to charge the energy storage component and to suitably supply the implant with power.

More precisely, the invention proposes an autonomous cardiac implant of the leadless capsule type including, in a manner known per se, in particular from the Published PCT Request WO 2012/020034 A1 mentioned hereinabove:
  an electronic unit, with a stimulation circuit adapted to deliver stimulation pulses to an electrode of the implant, in a controlled manner, as a function of at least one stimulation parameter;
  an energy storage component for powering the electronic unit;
  a circuit for evaluating a charge level of the energy storage component;
  a comparator, for comparing said charge level with a predefined lower threshold, and delivering conditionally a low charge indicator as a function of the comparison result; and
  an energy harvesting module, adapted to convert into electrical energy external stresses applied to the implant body under the effect of movements of a wall to which the implant is anchored and/or of blood flow rate variations in the environment surrounding the implant at the heartbeat rhythm and/or of cardiac tissue vibrations.

The energy harvesting module includes: an inertial unit subjected to said external stresses; a transducer adapted to convert the mechanical energy produced by the oscillations of the inertial unit into an electrical signal; and a power management circuit, adapted to rectify and regulate said electrical signal, to deliver as an output a stabilized direct voltage or current, for powering said electronic unit and/or charging said energy storage component.

Characteristically of the invention, the electronic unit further includes a dynamic charging control circuit, receiving as an input the low charge indicator and coupled at its output to the stimulation circuit, and adapted to modify said at least one stimulation parameter in a direction liable to increase the mean level of said mechanical energy produced by the inertial unit and converted by the transducer for powering said electronic unit and/or for charging said energy storage component.

According to various advantageous subsidiary characteristics:
  the inertial unit includes a pendular unit with an element elastically deformable according to at least one degree of freedom, coupled to an inertial mass;
  the energy harvesting module includes at least one piezoelectric plate coupled at one end to the inertial mass, said piezoelectric plate forming both said elastically deformable element and said transducer;
  the charge level of the energy storage component is a voltage measured at the terminals of the energy storage component;
  the dynamic charging control circuit is conditionally activated only when the low charge indicator is delivered by the comparator;
  the modified stimulation parameter is: a modified stimulation rate, wherein the stimulation rate can in particular be modified by a predetermined quantity or rate with respect to a reference rate, possibly progressively, by successive pitches; a modified voltage and/or a modified duration of the stimulations pulses; and/or the application of stimulation pulses to a cardiac cavity even in presence of spontaneous contractions of this cavity;

the modified stimulation rate may be a rate increased above a natural sinus rhythm of the patient (to boost the stimulation), or a rate reduced below this natural sinus rhythm (to allow the spontaneous rhythm to emerge);

the dynamic charging control circuit is conditionally activated only after detection of a predetermined patient's state, the implant then advantageously including an activity sensor, and/or means for analysing the variations of the electrical signal delivered by the transducer, adapted to deliver a signal representative of a predetermined state of activity of the patient and/or a signal representative of a predetermined pathological state of the patient;

a first timer adapted to deactivate the modification of said at least one stimulation parameter after a predetermined time period has elapsed following an activation of the dynamic charging control circuit, and/or a second timer adapted to prevent, before a predetermined time period has elapsed, any reactivation of the dynamic charging control circuit after a previous activation of the latter, and/or a means for deactivating the dynamic control circuit when said charge level reaches a predefined upper threshold, are provided.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

An exemplary embodiment of the device of the invention will now be described.

As regards its software aspects, the invention may be implemented by a suitable programming of the control software of a known cardiac stimulator device, for example a stimulator of the endocavitary leadless capsule type.

These devices include a programmable microprocessor or microcontroller coupled to circuits for receiving, shaping and processing electrical signals collected by electrodes arranged on the capsule, at least one of which is in contact with the myocardium, and delivering stimulation pulses to these electrodes. The adaptation of these devices to make the invention is within the reach of the one skilled in the art, and won't be described in detail. In particular, the software programs stored in memory and executed may be adapted or used to implement the functions of the invention that will be described hereinafter.

The method of the invention is indeed mainly implemented by software means, using suitable algorithms executed by a microcontroller or a digital signal processor. For the sake of clarity of the presentation, the various processing applied will be decomposed and schematized by a certain number of distinct functional modules or blocks and/or of interconnected circuits, but this representation has nevertheless only an illustrative character, these functions or circuits including common elements, corresponding in practice to a plurality of functions wholly executed by a single software.

Figure 1:
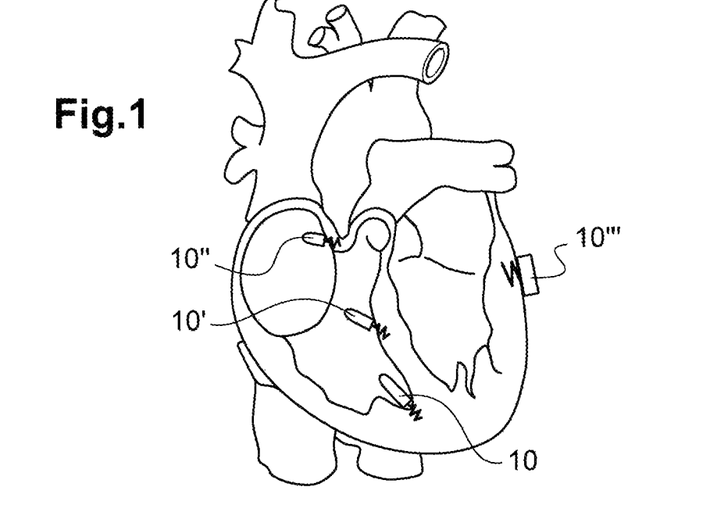
FIG. 1 illustrates a medical device of the leadless capsule type in its environment, with various examples of implantation sites in, on or near the heart of a patient.

In FIG. 1 are shown various possibilities of sites for implantation of a device of the leadless type, inside the myocardium (endocavitary implant) or on an external area of this same myocardium (epicardial implant), or also on or in a vessel close to the heart. In an advantageous preferential example, the leadless capsule 10 is implanted at the apex of the right ventricle. As a variant, the capsule may also be implanted on the right interventricular septum, as in 10', or on a wall of the right atrial cavity, as in 10". Another configuration consists, as in 10''', in implanting the leadless capsule on an outer wall of the myocardium.

In any case, the leadless capsule is fixed to the cardiac wall by means of a protruding anchoring system intended to enter the cardiac tissue for the holding on the implantation site. Other anchoring systems may be used and modify in no way the implementation of the present invention.

Figure 2:
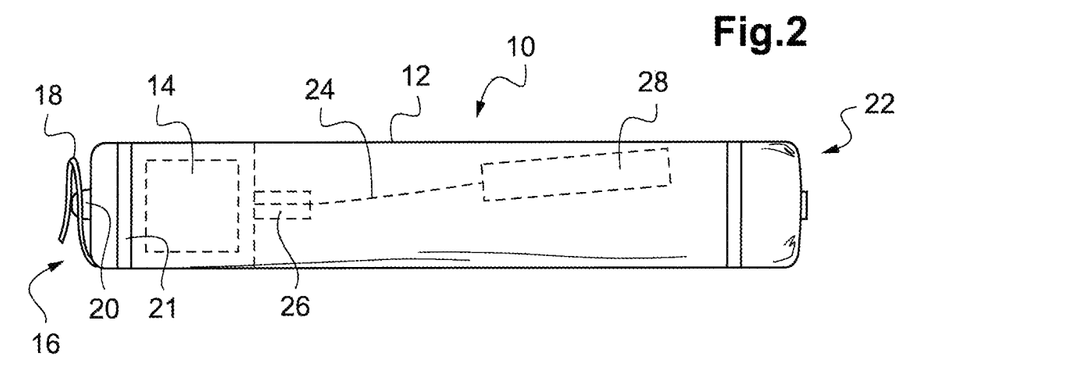
FIG. 2 is a generally longitudinal view of a leadless capsule including an energy harvester with a pendular unit.

FIG. 2 is a general longitudinal view of such a leadless capsule, including an energy harvester with a pendular unit.

The leadless capsule 10 is in this example made in the external form of a cylindrical tubular implant body 12 enclosing a unit 14 including the various electronic and power supply circuits of the capsule. The typical dimensions of such a capsule are a diameter of the order of about 6 mm over a length of about 25 mm.

At its distal end 16, the capsule carries a helical screw 18 for the anchoring of the capsule against a wall of a cardiac cavity, as illustrated hereinabove as regards FIG. 1. A detection/stimulation electrode 20, in contact with the cardiac tissue at the implantation site, collects the cardiac depolarization potentials and/or the application of stimulation pulses. In certain embodiments, the function of the electrode 20 is provided by the anchoring screw 18, which is then an active screw, electrically conductive and connected to the detection/stimulation circuits of the capsule. The electrode 20 in contact with the tissues is generally a cathode, and is associated with an anode whose function is provided by a second remote electrode, most often an annular electrode as in 21.

The opposite proximal end 22 of the leadless capsule 10 has an atraumatic rounded shape and is provided with suitable gripping means for the connection to a guiding catheter or other implantation accessory usable at the time of positioning or explanting the capsule.

The leadless capsule 10 is provided with an energy harvesting module intended to power the electronic unit 14 and to charge an integrated energy storage component.

Such an energy harvesting module includes an inertial unit that, inside the capsule, oscillates according to the various external stresses to which the leadless capsule is subjected. These stresses may result in particular from: movements of the wall to which the capsule is anchored, which are transmitted to the implant body 12 by the anchoring screw 18; and/or blood flow rate variations in the environment surrounding the implant, which produce oscillations of the implant body at the heartbeat rhythm; and/or various vibrations transmitted by the cardiac tissues.

Figure 3:
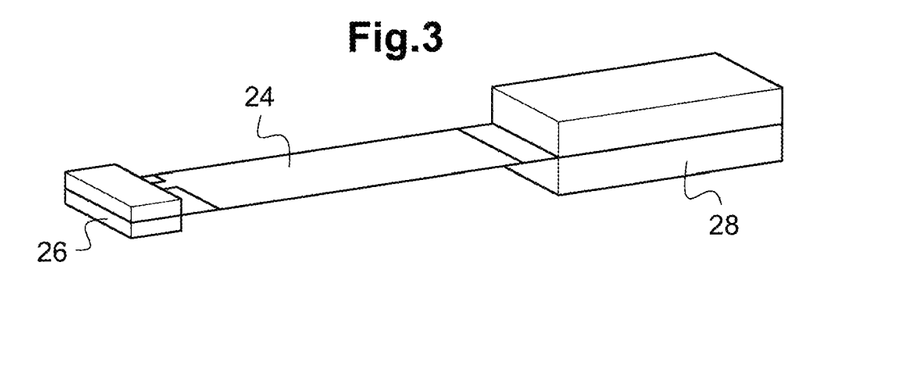
FIG. 3 shows separately the pendular unit of the leadless capsule of FIG. 2, with a piezoelectric plate coupled to an inertial mass.

FIG. 3 illustrates an example of an inertial unit for an energy harvesting module, a unit that is herein made up of a piezoelectric plate 24 fitted at one end 26 and whose opposite, free end is coupled to the inertial mass 28. The piezoelectric plate 24 is a flexible plate that, in the illustrated example, is elastically deformable according to at least one degree of freedom in longitudinal flexion.

From the mechanical point of view, this unit constitutes a pendular system of the mass-spring type (the spring being made up from the flexible piezoelectric plate) that, due to the inertia of the mass 28, oscillates as soon as the elastic plate 24 is spaced apart from its stable rest position. De facto, this unit may be likened, as regards its mechanical behaviour, to a structure of the "fitted-free beam" type, which has a natural frequency of free oscillation, which is herein the frequency at which the mass-spring system oscillates.

The piezoelectric plate 24 further provides a function of mechanical-electrical transducer for converting into electrical charges the mechanical stress that is applied thereto when it is flexed, said charges being collected by electrodes formed at the surface of the plate. The plate is preferably a plate of the bimorphous type, i.e. capable of generating energy on its two faces when subjected to a deformation. These transduction properties are typical of a piezoelectric material such as the PZT ceramics or the monocrystals of the PMN-PT, barium titanate or lithium niobate type.

Of course, the invention is not limited to this particular configuration of pendular unit given as an example, and other types of inertial units may be used for the energy harvesting, such as those mentioned in introduction, from the moment that they have at least one natural frequency of free oscillation.

Likewise, the inertial unit may be a unit deformable according to several degrees of freedom, with then as much corresponding vibratory modes and natural frequencies of oscillation, and of electrical signals respectively delivered at the output.

Figure 4:
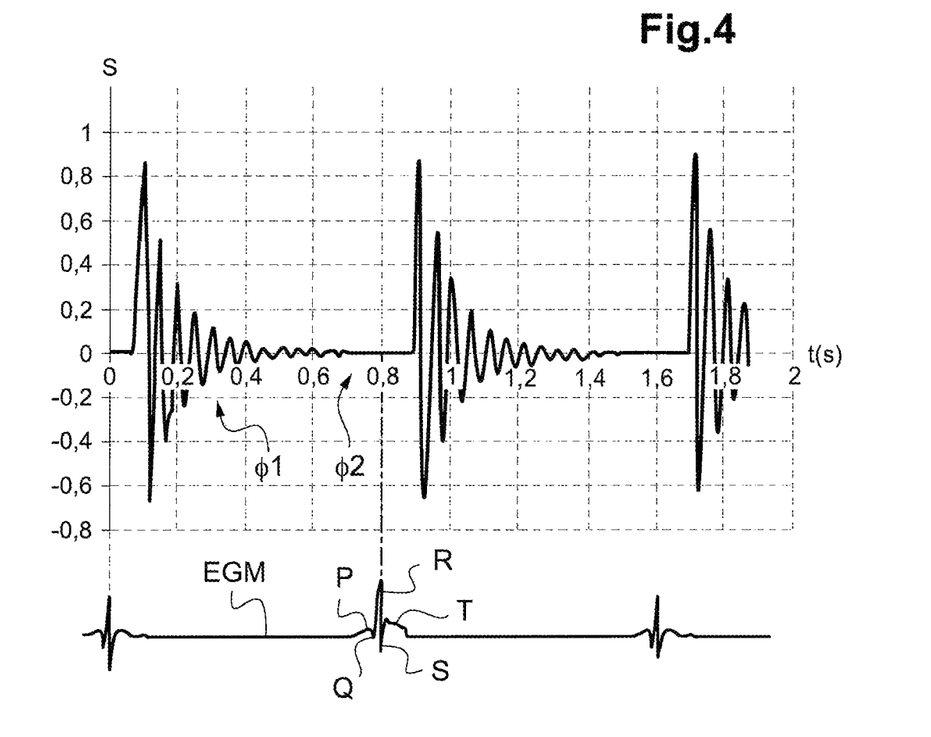
FIG. 4 is a chronogram of the oscillations of the electrical signal delivered by the energy harvesting module of the leadless capsule during successive cardiac cycles, alongside with the corresponding electrogram pattern.

FIG. 4 is a chronogram of the oscillations of the electrical signal S delivered by the energy harvesting module of the leadless capsule during successive cardiac cycles, alongside with the corresponding electrogram pattern.

The electrogram signal EGM, which is the electrical signal of the cardiac depolarization wave, is for example detected by the electrode 20 in contact with the myocardium. In the example illustrated in FIG. 4, the electrogram is that of a sinus rhythm, with a wave P corresponding to the atrial electrical activity, a QRS complex corresponding to the ventricular electrical activity and a wave T corresponding to the ventricular repolarization.

FIG. 4 also illustrates, alongside the electrogram EGM, the variations of the electrical signal S delivered by the energy harvester, i.e. the variable signal produced by the mechanical-electrical transducer made up by the piezoelectric plate 24, in the illustrated example.

This signal is a recurrent signal, repeated at the rhythm of the successive cardiac heartbeats, and it includes at each occurrence two characteristic phases following each other, $\sqrt{o}1$ and $\sqrt{o}2$.

The first phase $\sqrt{o}1$ includes a series of damped sinusoidal oscillations, with a first amplitude peak followed with a series of "bounces" of decreasing amplitudes, and it is followed with a second, consecutive phase $\sqrt{o}2$, substantially without bounce, which continues until a new contraction of the myocardium producing similar variations of the signal S.

The order of magnitude of the recurrence rate of the cardiac cycles is typically of 1 to 2 Hz (60 to 120 bpm (beats per minute)). The natural frequency of the pendular unit is determined by the geometry of the piezoelectric plate 24 (mainly its length and thickness), by the elasticity of the material that composes it, and by the mass of the inertial mass 28. These different parameters may be advantageously chosen so as to give the natural frequency of free oscillation a value that is far higher than that of the cardiac rhythm, for example a rate of the order of 20 Hz, this value being of course not limitative. Almost in all circumstances, the pendular unit will then produce between two heartbeats a plurality of bounces followed by a phase with no bounces before the following heartbeat.

Figure 5:
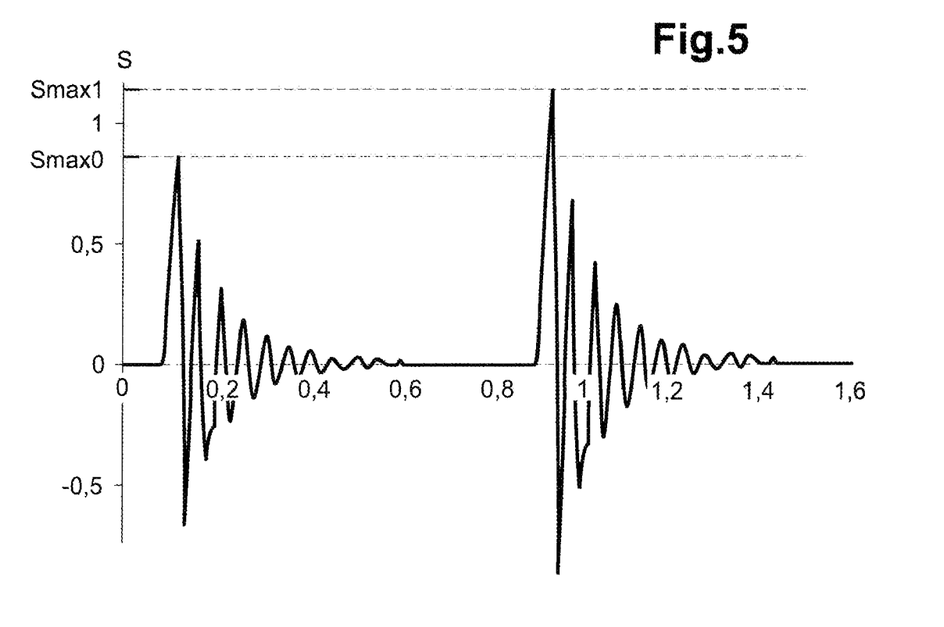
FIG. 5 is homologous to FIG. 4, for two successive cardiac cycles, the first one corresponding to a spontaneous contraction of the myocardium and the second one to a stimulated contraction of this same myocardium, resulting from the application of the latter to an electrical stimulation pulse.

FIG. 5 is a comparative chronogram of the oscillations of the electrical signal S delivered by the energy harvesting module of the capsule for a first cycle corresponding to a spontaneous event (natural contraction of the myocardium, without external stimulation) and for a second cycle corresponding to a stimulated event (contraction produced after the application of an electrical stimulation pulse generated by the leadless capsule).

It will be noted that the main amplitude peak Smax0 of the signal collected at the time of a spontaneous contraction is lower than the corresponding peak Smax1 of the signal collecting at the time of a stimulated contraction. The peaks of the following bounces are also of lower amplitude. Consequently, the mechanical energy collected and transformed into electrical energy by the energy harvesting module (energy that is approximately proportional to the root mean square (RMS) value of the signal S integrated over the duration of a cycle) will also be lower.

Moreover, whether the rhythm is spontaneous or stimulated, the electrical energy produced over a given duration by the energy harvester will be lower when this rhythm is slow than when this rhythm is fast, due to a lower repetition rate of the individual events producing charging current.

The basic idea of the invention resides in monitoring the charge level of the energy storage component and, if the latter falls below a minimum threshold, acting on the operation of the implant so as to produce in response stimulated contractions that are mechanically more productive and that, consequently, allow a greater quantity of electrical energy to be harvested for charging the energy storage component.

This stimulation modified in response to the detection of the low charge level may be performed in various ways, in particular:

by delivering stimulation pulses though the myocardium can contract spontaneously (which has for effect to increase the amplitude of the mechanical oscillations and hence those of the electrical signal collected—situation illustrated in FIG. 5); and/or by increasing the stimulation rate, i.e. by forcing the heart to beat slightly faster; and/or by producing electrical stimulation pulses of higher amplitude (voltage or current) and/or of larger pulse width.

Figure 6:
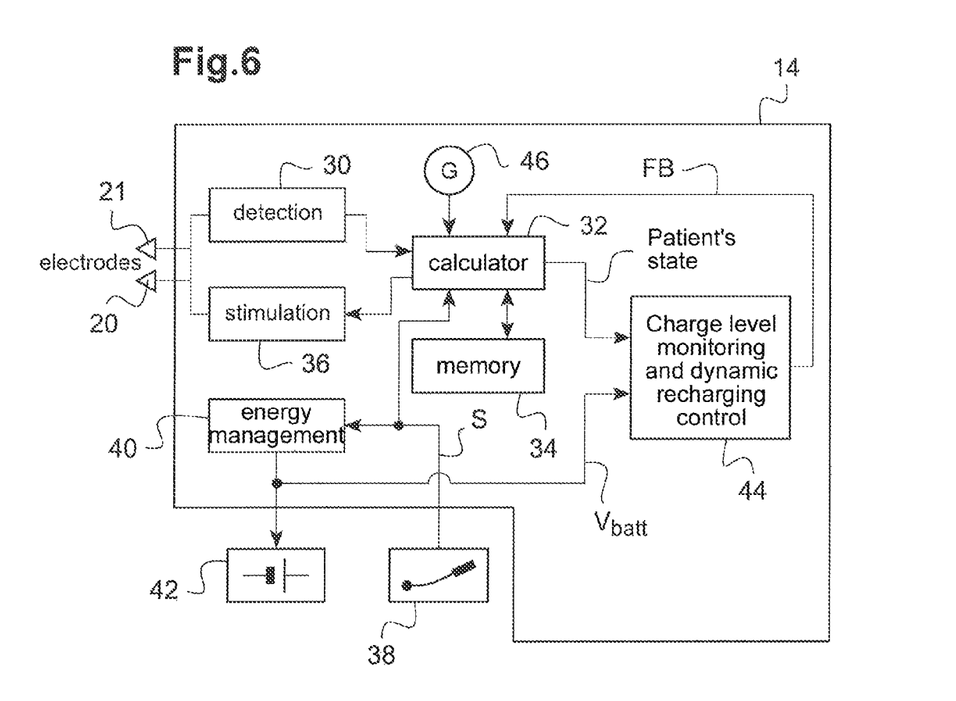
FIG. 6 shows, as a block diagram, the main internal constitutive elements of the electronic unit of the leadless capsule.

FIG. 6 is a synoptic representation of the electronic unit 14 integrated into the leadless capsule 10, shown as functional blocks. This circuit 14 is advantageously implemented as an ASIC or a combination of ASICs.

Block 30 denotes a circuit for detecting the cardiac depolarization wave, connected to the electrode 20 in contact with the cardiac tissue and to the opposite electrode 21. Block 30 includes filters and means for analog and/or digital processing of the signal collected. The so-processed signal is applied to the input of a calculator 32 associated with a memory 34. The electronic unit 14 also includes a stimulation circuit 36 operating under the control of the calculator 32 for, as and whenever necessary, delivering myocardium stimulation pulses to the system of electrodes 20 and 21.

An energy harvesting circuit 38 is moreover provided, made up by the pendular unit formed by the piezoelectric plate 24 and the inertial mass 28 described hereinabove with reference to FIGS. 2 and 3.

This energy harvesting circuit 38 produces as an output a variable electrical signal S such as that of FIGS. 4 and 5 described hereinabove.

First, the signal S is delivered to a power management circuit 40, which rectifies and regulates the signal S so as to produce as an output a stabilized direct voltage or current used for powering the electronic unit 14 and charging the energy storage component 42, which itself powers the electronic unit 14. The signal S has also sent to the calculator, in order to deduce therefrom information about the physiological/pathological state of the patient.

Characteristically of the invention, the electronic unit 14 also includes a module 44 for monitoring the charge level and for dynamically controlling the charging of the energy storage component 42.

This module 44 receives as an input, on the one hand, a signal representative of the current charge level of the energy storage component. In its simplest version, this signal is a voltage level signal Vbatt across the terminals of the energy storage component 42. Other more complex techniques may also be implemented, such as those used in portable phones, for example including a circuit for energy storage component management.

The module 44 receives as an input, on the other hand, a signal representative of the current patient's state, yield by calculator 32, in particular based on the information outputted by an activity sensor 46 such as an acceleration sensor or "G-sensor" incorporated to the circuits of the leadless implant. The calculator may also determine information about the patient's state based on signal S. It will be noted that, by "patient's state", it is meant an indication representative of the state in which the patient is at a given instant among several possible states, such as: activity/sleep/rest/wake, etc., this set of possible states being predetermined states or states set up by the physician. In a more advanced version of the invention, the state may take into account the patient's clinical status (arrhythmia, loss of activity, etc.), diagnosed over a longer or shorter duration (daily, weekly, etc.).

As a function of the combined information of charge level of the energy storage component (voltage Vbatt) and of current patient's state, the module 44 delivers as a response a feedback signal FB applied to the calculator 32, which will have for effect, in case of low charge level, to modify one or several stimulation parameters so as to increase the mechanical energy produced by the heart, and, consequently, the electric energy produced by the harvesting module.

Figure 7:
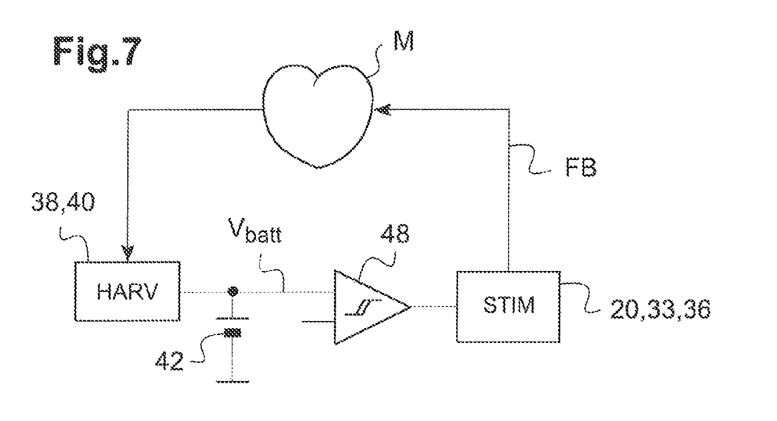
FIG. 7 schematically illustrates the principle of the invention.

FIG. 7 schematically illustrates the principle of the invention, which resides in creating a feedback loop between the myocardium M, the energy harvesting circuit 38, 40 and the stimulation circuits 20, 32 and 36.

The charge level Vbatt of the energy storage component 42, charged by the energy harvesting circuit 38, 40, is compared with a lower threshold (comparator 48) to conditionally control the stimulation circuits 20, 32, 36 and to apply in return an increased stimulation FR to the myocardium M.

The boosted stimulation of the myocardium is operated according to the various techniques mentioned hereinabove: forced stimulation, even when the myocardium has the capacity to contract spontaneously, and/or increase of the stimulation rate, and/or increase of the stimulation pulse energy (by increasing the amplitude and/or the duration of this pulse).

Advantageously, the comparator 48 also compares the charge level Vbatt with an upper threshold, to interrupt the application of a boosted stimulation when the level of the energy storage component has increased above a sufficient charge level.

Figure 8:
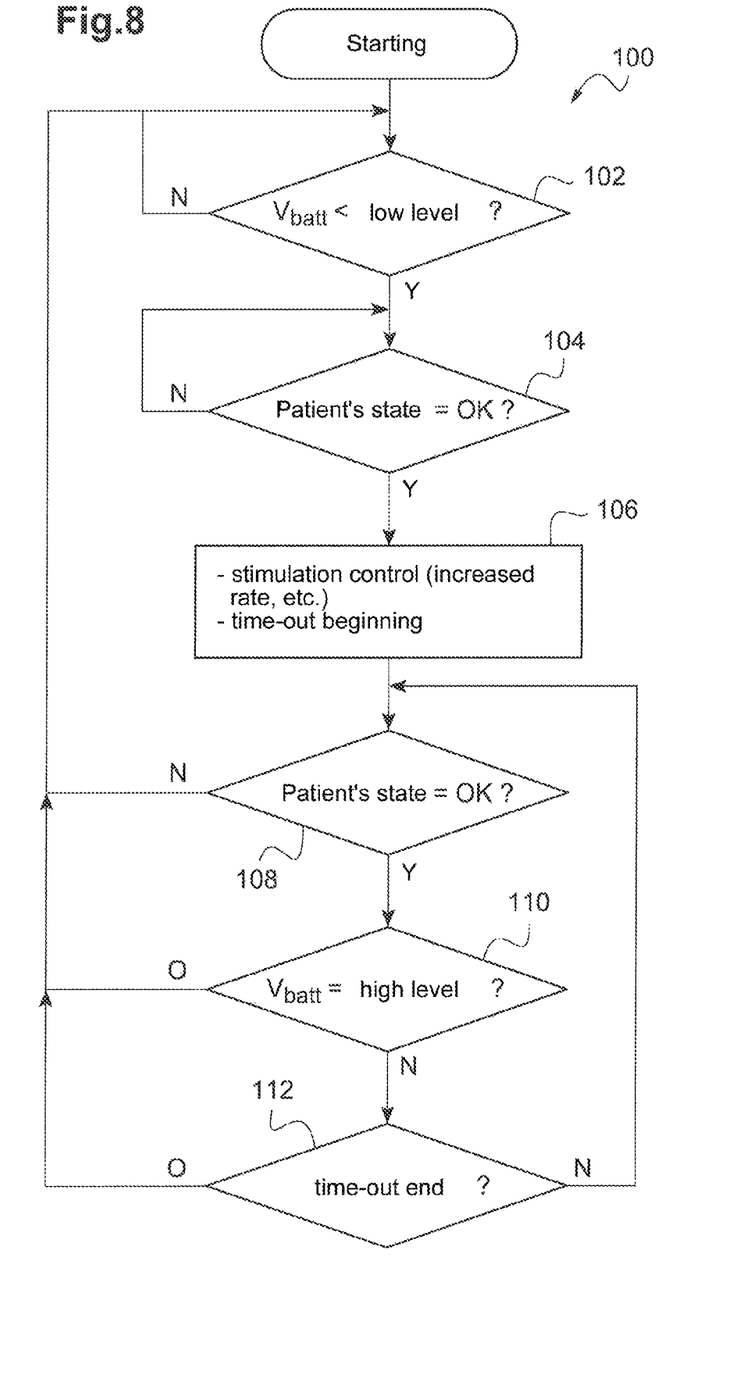
FIG. 8 is a flow diagram detailing the sequence of operations and tests of a first illustrative example of implementation of the invention, with application of a boosted stimulation to the patient.

FIG. 8 is a flow diagram 100 detailing a first illustrative example of a sequence of operations and tests for the implementation of the invention, providing the application of a boosted stimulation to the patient.

In test 102, the voltage of the energy storage component is compared to a predetermined lower threshold level. If the voltage is lower than this threshold level, the current patient's state is then examined (test 104) so as to continue the process only in situations that are not cumbersome for the patient. For example, it will be considered that the patient's state allows the process to be continued if the state is "patient not active and not asleep".

The boosted stimulation is then implemented (block 106) by a suitable control of the calculator 32 for controlling the application of a stimulation as desired. For example, the stimulation rate is controlled at a value equal to that of the sinus rhythm (SR) increased by 10 bpm. Moreover, a first time-out period is initialized and triggered.

At the following step (block 108), the patient's state is checked again. If the patient's state still allows the boosted stimulation process to be continued, the latter is continued up to the moment when the level Vbatt of the energy storage component reaches a predetermined high level (test 110), or the moment when the process arrives at the end of the first time-out period triggered at step 106 (test 112), so as to limit in time the application of a boosted stimulation.

Different variants or complements of this process may be contemplated, for example:
- the boosted stimulation may be applied even if the patient's state is "in activity". The stimulation rate, which is calculated based on data provided by a sensor (so-called rate-adaptive stimulation) is then increased by a predetermined quantity, for example of 10 bpm, or a predetermined rate, for example of 5 or 10%;
- the increase of the stimulation rate may be operated by increasing successive pitches, for example the rate is increased by 1 bpm at each minute up to a maximum increase value, for example a value of 15 bpm;
- at the end of the first time-out period, a second time-out period may be triggered, which inhibits the process so as to prevent any reactivation of the latter before a predetermined time period has elapsed.

Figure 9:
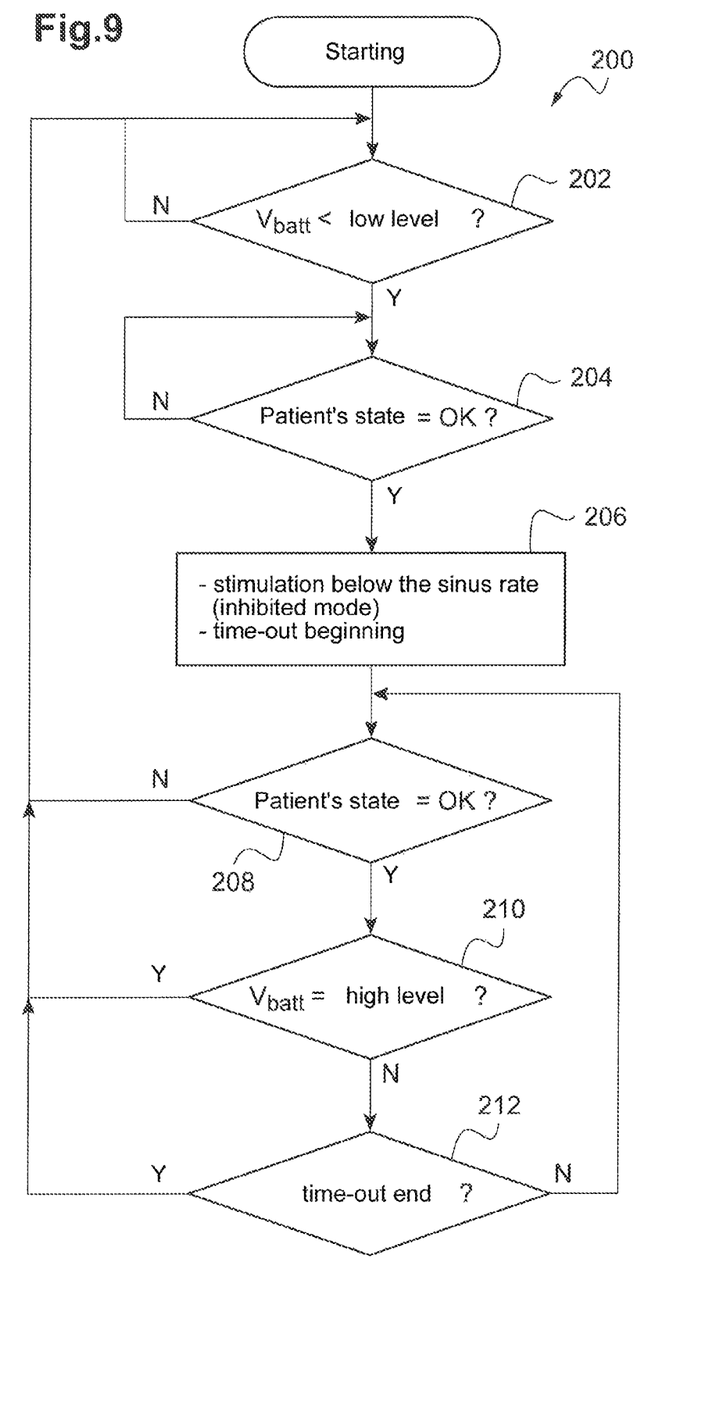
FIG. 9 is a flow diagram homologous to that of FIG. 8, for a second illustrative example, with inhibition of the stimulation applied to the patient.

FIG. 9 is a flow diagram 200, homologous to that of FIG. 8, for a second illustrative example, no longer providing the application to the patient of a boosted stimulation but, on the contrary, a mode in which the stimulation is inhibited, to allow a spontaneous rhythm to be expressed.

In test 202, the voltage of the energy storage component is compared to the predetermined lower threshold level. If the voltage is lower that this threshold level, the current patient's state is then examined (test 204) so as to continue the process only in situations that are not cumbersome for the patient. For example, it will be considered that the patient's state allows the process to be continued if the state is "patient not active and not asleep".

The stimulation is then deactivated by application of a stimulation rate lower than the patient's (spontaneous) sinus rhythm (block 206), by a suitable control of the calculator 32 that controls the application of the stimulation. For example, the stimulation rate is controlled at a value equal to that of the patient's natural sinus rhythm (SR), reduced by 10 bpm. Moreover, a first time-out period is initialized and triggered.

At the following step (block 208), the patient's state is checked again. If the patient's state still allows the inhibited stimulation process to be continued, the latter is continued up to the moment when the level Vbatt of the energy storage component reaches a predetermined high level (test 210), or the moment when the process arrives at the end of the first time-out period triggered at step 206 (test 212), so as to limit in time the application of a inhibited stimulation.

Here again, at the end of the first time-out period, a second time-out period may be triggered, which inhibits the process so as to prevent any reactivation of the latter before a predetermined time period has elapsed.

Figure 10:
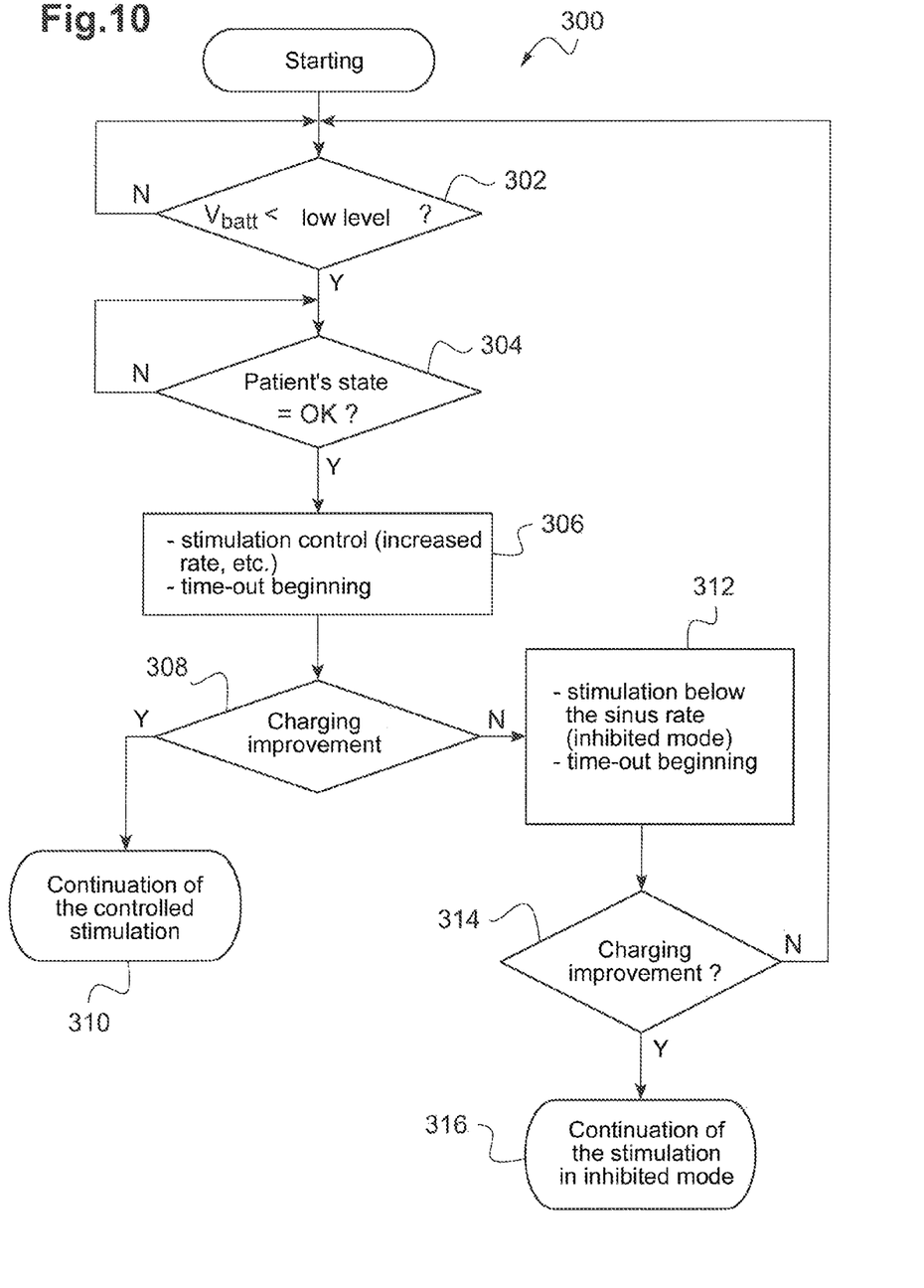
FIG. 10 is a flow diagram detailing a sequence of operations and tests for an automatic determination between boosted stimulation and inhibition of the stimulation.

FIG. 10 is a flow diagram 300 detailing a sequence of operations and tests for an automatic determination between boosted stimulation approach (as in the case of FIG. 8) or an approach by inhibition of the stimulation (as in the case of FIG. 9).

In test 302, the voltage of the energy storage component is compared to a predetermined lower threshold level. If the voltage is lower than this threshold level, the current patient's state is then examined (test 304) so as to continue the process only in situations that are not cumbersome for the patient. For example, it will be considered that the patient's state allows the process to be continued if the state is "patient not active and not asleep".

The boosted stimulation is then implemented (block 306), by a suitable control of the calculator 32 for controlling the application of a stimulation as desired. For example, the stimulation rate is controlled at a rate equal to that of the patient's natural sinus rhythm (SR), increased by 10 bpm. Moreover, a first time-out period is initialized and triggered, as in the case of the blocks 106 and 206 described hereinabove as regards FIGS. 8 and 9.

At the following step (test 308), the efficiency of the stimulation rate increase is tested, in order to determine if the latter had a positive effect on the signal of the energy harvester.

If the efficiency is proved (over one or several cardiac cycles), the charging strategy using a stimulation rate increase is kept (block 310); otherwise, the stimulation rate is reduced below the patient's natural sinus rhythm, in order to test the inhibited mode (block 312). In test 314, if the efficiency is proved (over one or several cardiac cycles), the charging strategy using a stimulation inhibition is kept (block 316); otherwise, the process is abandoned and the system goes back to the starting state, corresponding to test 302.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

I claim:

1. An autonomous cardiac implant of a leadless capsule type comprising an implant body provided with means for anchoring to a cardiac wall of a heart and comprising:
   an electronic unit, with a stimulation circuit adapted to deliver stimulation pulses to an electrode of an implant, in a controlled manner, as a function of at least one stimulation parameter;
   an energy storage component for powering the electronic unit;
   a circuit for evaluating a charge level of the energy storage component;

a comparator, for comparing said charge level with a predefined lower threshold, and delivering conditionally a low charge indicator as a function of a comparison result of the comparing; and an energy harvesting module, adapted to convert external stresses applied to the implant body into electrical energy under an effect of movements of a wall to which the implant is anchored and/or of blood flow rate variations in an environment surrounding the implant at a heartbeat rhythm and/or of cardiac tissue vibrations the energy harvesting module comprising:

an inertial unit subjected to said external stresses;

a transducer adapted to convert mechanical energy produced by oscillations of the inertial unit into an electrical signal; and a power rectifier and regulator delivering as an output a stabilized direct voltage or current, for powering said electronic unit and/or charging said energy storage component, wherein the electronic unit further comprises:

a dynamic charging control circuit, receiving as an input the low charge indicator and coupled at its output to the stimulation circuit, and adapted to modify said at least one stimulation parameter to a rate above a natural sinus rhythm of a patient thereby boosting stimulation to the heart, resulting in an increase in a mean level of said mechanical energy produced by the inertial unit and converted by the transducer for powering said electronic unit and/or for charging said energy storage component, the comparator comparing said charge level with an upper threshold, and the dynamic charging control circuit interrupting the delivery of the stimulation pulses when the charge level has increased above the upper threshold.

2. The implant of claim 1, wherein the inertial unit comprises a pendular unit with an elastically deformable element with at least one degree of freedom, coupled to an inertial mass.

3. The implant of claim 2, wherein the energy harvesting module comprises at least one piezoelectric plate coupled at one end to the inertial mass, said piezoelectric plate forming both said elastically deformable element and said transducer.

4. The implant of claim 1, wherein the charge level of the energy storage component is a voltage measured at terminals of the energy storage component.

5. The implant of claim 1, wherein the dynamic charging control circuit is conditionally activated only when the low charge indicator is delivered by the comparator.

6. The implant of claim 1, wherein said at least one modified stimulation parameter is a modified stimulation rate.

7. The implant of claim 6, wherein the modified stimulation rate is modified by a predetermined quantity or rate with respect to a reference rate.

8. The implant of claim 6, wherein the modified stimulation rate is progressively modified, by successive pitches.

9. The implant of claim 1, wherein said at least one stimulation parameter modified in the direction is a modified voltage and/or a modified duration of stimulation pulses.

10. The implant of claim 1, wherein said at least one stimulation parameter modified in the direction is an application of stimulation pulses to a cardiac cavity even in the presence of spontaneous contractions of this cavity.

11. The implant of claim 1, wherein the dynamic charging control circuit is conditionally activated only after detection of a predetermined state of a patient.

12. The implant of claim 11, wherein the implant comprises an activity sensor adapted to deliver a signal representative of a predetermined state of activity of the patient and/or a signal representative of a predetermined pathological state of a patient.

13. The implant of claim 11, further comprising means for analysing variations of the electrical signal delivered by the transducer, adapted to deliver a signal representative of a predetermined state of activity of the patient and/or a signal representative of a predetermined pathological state of a patient.

14. The implant of claim 1, wherein it is provided a first timer adapted to deactivate a modification of said at least one stimulation parameter after a predetermined time period has elapsed following an activation of the dynamic charging control circuit.

15. The implant of claim 1, wherein it is provided a second timer adapted to prevent, before a predetermined time period has elapsed, any reactivation of the dynamic charging control circuit after a previous activation of the dynamic charging control circuit.

* * * * *